Figure 1:
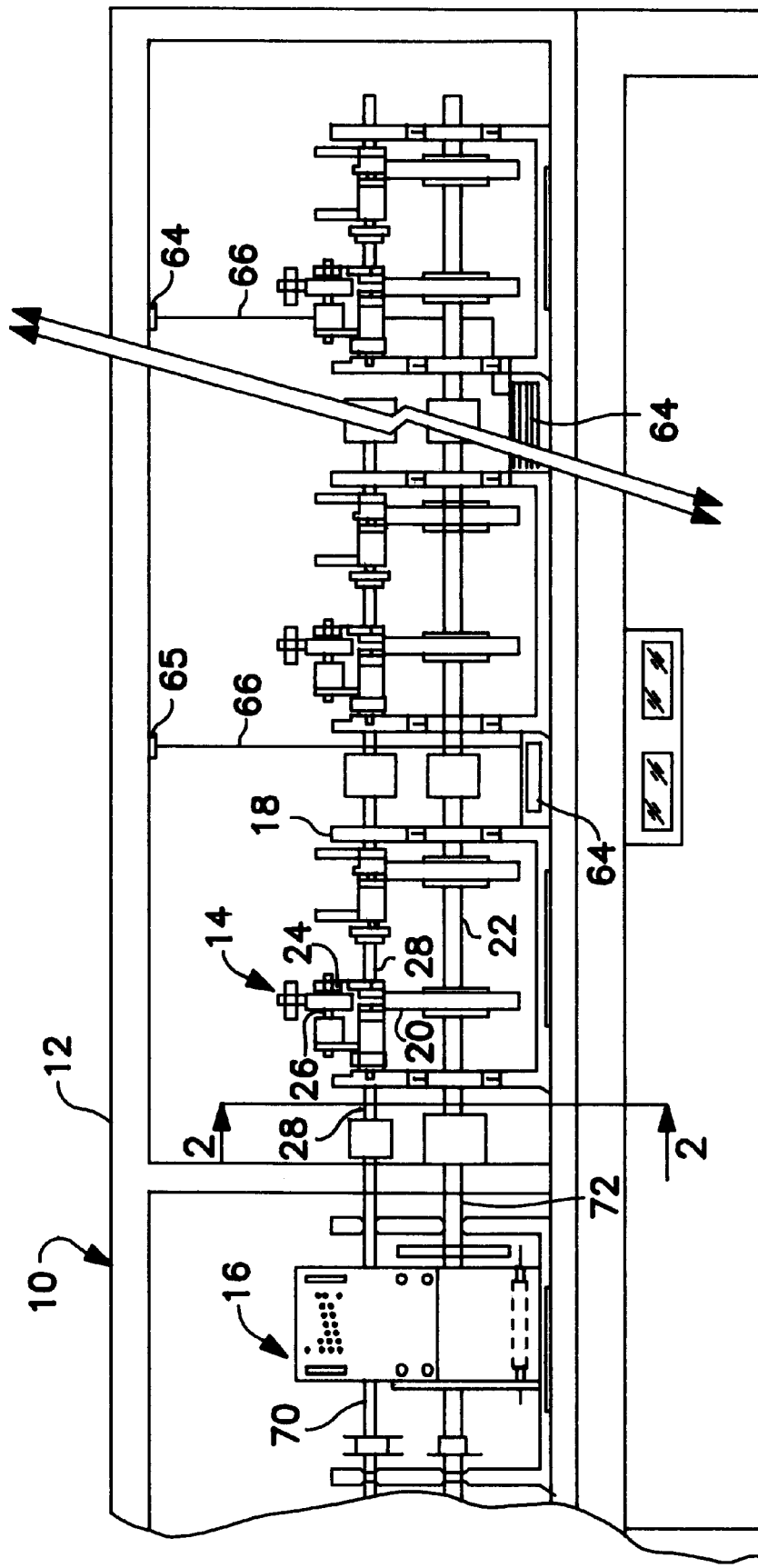

United States Patent [19]
Ouyang et al.

[11] Patent Number: 6,050,876
[45] Date of Patent: Apr. 18, 2000

[54] AUTOMATED ABRADER

[75] Inventors: George Ouyang, Lexington; Stanley L. Markowitz, Framingham; Gary K. Wolfrom, Rockport; Maurice J. Bedard, Lowell; Lawrence A. Roy, Marlboro, all of Mass.

[73] Assignee: Cabot Corporation, Boston, Mass.

[21] Appl. No.: 08/907,712

[22] Filed: Aug. 8, 1997

[51] Int. Cl.[7] .................................................. B24B 49/00
[52] U.S. Cl. .................................. 451/5; 451/6; 451/254
[58] Field of Search ..................................... 451/5, 6, 254

[56] References Cited

U.S. PATENT DOCUMENTS

| | | |
|---|---|---|
| 1,875,786 | 9/1932 | Warner . |
| 2,010,049 | 8/1935 | Abbott, Jr. et al. . |
| 3,152,468 | 10/1964 | Powell . |
| 3,553,903 | 1/1971 | Christie . |
| 3,574,973 | 4/1971 | Rader . |
| 3,604,245 | 9/1971 | Atelian . |
| 3,726,124 | 4/1973 | Obarski . |
| 3,835,591 | 9/1974 | Cimprich ............................... 51/106 R |
| 3,848,368 | 11/1974 | Toshioka et al. ...................... 51/165 R |
| 3,899,917 | 8/1975 | Kisbany . |
| 3,977,243 | 8/1976 | Yamada et al. . |
| 4,036,607 | 7/1977 | Freddi . |
| 4,084,350 | 4/1978 | Ongaro .................................. 51/106 R |
| 4,095,374 | 6/1978 | Ugo . |
| 4,128,969 | 12/1978 | Gormish et al. . |
| 4,233,838 | 11/1980 | Stiebel . |
| 4,359,896 | 11/1982 | Brown, Jr. et al. . |
| 4,674,326 | 6/1987 | Reinecke . |
| 4,704,900 | 11/1987 | Beebe . |
| 4,748,988 | 6/1988 | Green et al. . |
| 4,805,125 | 2/1989 | Beebe . |
| 4,837,980 | 6/1989 | Rogers, Jr. . |
| 4,873,793 | 10/1989 | Asano et al. .......................... 51/165.71 |
| 4,995,197 | 2/1991 | Shieh et al. . |
| 5,357,799 | 10/1994 | Roth et al. . |
| 5,448,910 | 9/1995 | Yurjevich et al. . |
| 5,746,643 | 5/1998 | Terasaki et al. ............................ 451/5 |

FOREIGN PATENT DOCUMENTS 26 11 123   9/1977   Germany .

OTHER PUBLICATIONS

PCT International Search Report dated Nov. 18, 1998.
Patent Abstracts of Japan, vol. 095, No. 009, Oct. 31, 1995 & JP 07 146217 A (Sumitomo Rubber Ind. Ltd), Jun. 6, 1995 (see abstract).
P. Walraven, Laboratory Tread Wear Simulation, Oct. 17–20, 1995, Presented at a meeting of the Rubber Division, American Chemical Society, Cleveland, OH.

*Primary Examiner*—David A. Scherbel
*Assistant Examiner*—Dung Van Nguyen

[57] ABSTRACT

An automated apparatus for testing a plurality of sample wheels includes a grindstone, a first programmable servo motor coupled to the grindstone, a plurality sample wheels disposed about a circumference of the grindstone, and a second programmable servo motor coupled to each of the plurality of sample wheels. In addition, the automated apparatus also includes a controller that outputs a first control signal to the first programmable servo motor and a second control signal to the second programmable servo motor to provide a variable slip ratio between the grindstone and the plurality of sample wheels. The controller includes a simulator that simulates a plurality of road conditions and varies the plurality of slip ratios to simulate the plurality of road conditions. The automated apparatus also includes a first optical encoder that detects the angular velocity of the grindstone and that outputs a first signal and a plurality of second optical encoders that each detect the angular velocity of a corresponding sample wheel and output a second signal. The controller includes a processor that is responsive to the first output signal and the second output signal that computes, in situ, a free rolling diameter of each of the plurality of sample wheels. The processor also determines, in situ, a wear rate of each of the plurality of sample wheels. Moreover, the automated apparatus includes a variable powder delivery system that provides a uniform amount of aerosol powder to the interface of the grindstone and each of the plurality of sample wheels at a plurality of pumping rates to simulate variable road dust conditions.

20 Claims, 8 Drawing Sheets

AUTOMATED ABRADER

BACKGROUND OF THE INVENTION

1. Field of the Invention

The present invention relates to an automated abrader. In particular, the present invention relates to an apparatus for abrading tire tread compounds or other types of rubber compounds, to measure the wear rate, wear resistance and/or abrasion resistance of the compounds under simulated road wear conditions.

2. Discussion of the Related Art

Known methods and apparatus exist for abrading tire tread compounds or other types of rubber compounds. The apparatus generally include a moving abrasive surface. A sample of the compound to be abraded is engaged with the moving abrasive surface. The amount of material abraded from the sample is then measured to predict the wear rate, the wear resistance and/or the abrasion resistance of the tire tread compound of the sample under actual road conditions.

By way of example, some common laboratory abraders are the Lambourne abrader and the Akron angle abrader. The Lambourne abrader and the Akron angle abrader each test a solid rubber sample wheel by grinding the sample wheel against a grindstone wheel. In addition, each of these abraders uses a continuous slip between the grindstone wheel and the sample wheel. However, one problem with each of these laboratory abraders is that due to the continuous slip, the sample wheel surface can become significantly hotter than that of for example a radial tire which does not experience much slippage at the tire-to-road interface except during severe driving conditions such as braking, cornering or accelerating. For example, a 1987 American Chemical Society, Rubber Division Spring Meeting paper (No. 79) by Yoshi and Takeshita has shown that under continuous slip at 25% slip, the surface temperature of the solid rubber sample wheel rose to about 55° C. (from 30° C. ambient) in just one minute. This 25° C. rise in surface temperature is not a condition that would be experienced by a radial tire under actual road wear conditions and thus leads to errors in the tested performance of the sample wheel.

Another known apparatus and method is the Pico test wherein a rotating razor blade is continuously engaged against the sample wheel to scratch the sample wheel. However, results based upon the Pico test do not correlate well with actual results under actual road conditions and therefore the Pico test is not accepted by the tire industry. Still another test is the DIN test, wherein a drum covered with sandpaper is continuously engaged with the sample wheel to wear the sample wheel. However, the DIN test suffers from the same infirmities as the Pico test.

Another problem with each of the above the known abrading methods and apparatus is that the abrasion data is taken only at one continuous wear rate level or at most a few continuous wear rate levels, in order to determine an average level of abrasion severity. However, it is known in the industry that the tread wear characteristic of tires under actual road wear conditions may vary dramatically at different levels of abrasion severity. As a result, the related art abrading apparatus and methods that abrade at only one level, or at most a few levels of abrasion severity, don't correlate very well with actual wear rate, and the like, of tires under actual road conditions.

Still another problem that results from the related art methods and apparatus is that a tire tread compound may indicate excellent abrasion performance at the tested level of abrasion, but when used in a tire and subjected to varying road wear conditions such as, for example, with a performance car, the tire will likely exhibit a high wear rate and/or develop an irregular wear pattern. Tires that exhibit irregular wear patterns tend to substantially decrease the life of the tire.

Accordingly, it is desirable to test the abrasion characteristics of tire tread compounds under a variety of conditions to simulate actual road wear performance. However, none of the known methods and apparatus have the capability to simulate the variety of conditions of road wear performance. Therefore, the industry has resorted to testing the tire tread compounds on road vehicles under a variety of conditions in order to predict actual road wear performance. However, this is a time-consuming and expensive procedure.

One known abrading apparatus of the related art is disclosed in U.S. Pat. No. 4,995,197, herein incorporated by reference. FIG. 1 illustrates a partial front view of the abrading apparatus 10 disclosed in U.S. Pat. No. 4,995,197. The apparatus includes a plurality of test stations 14 and a drive module 16 that drives each test station.

Figure 2:
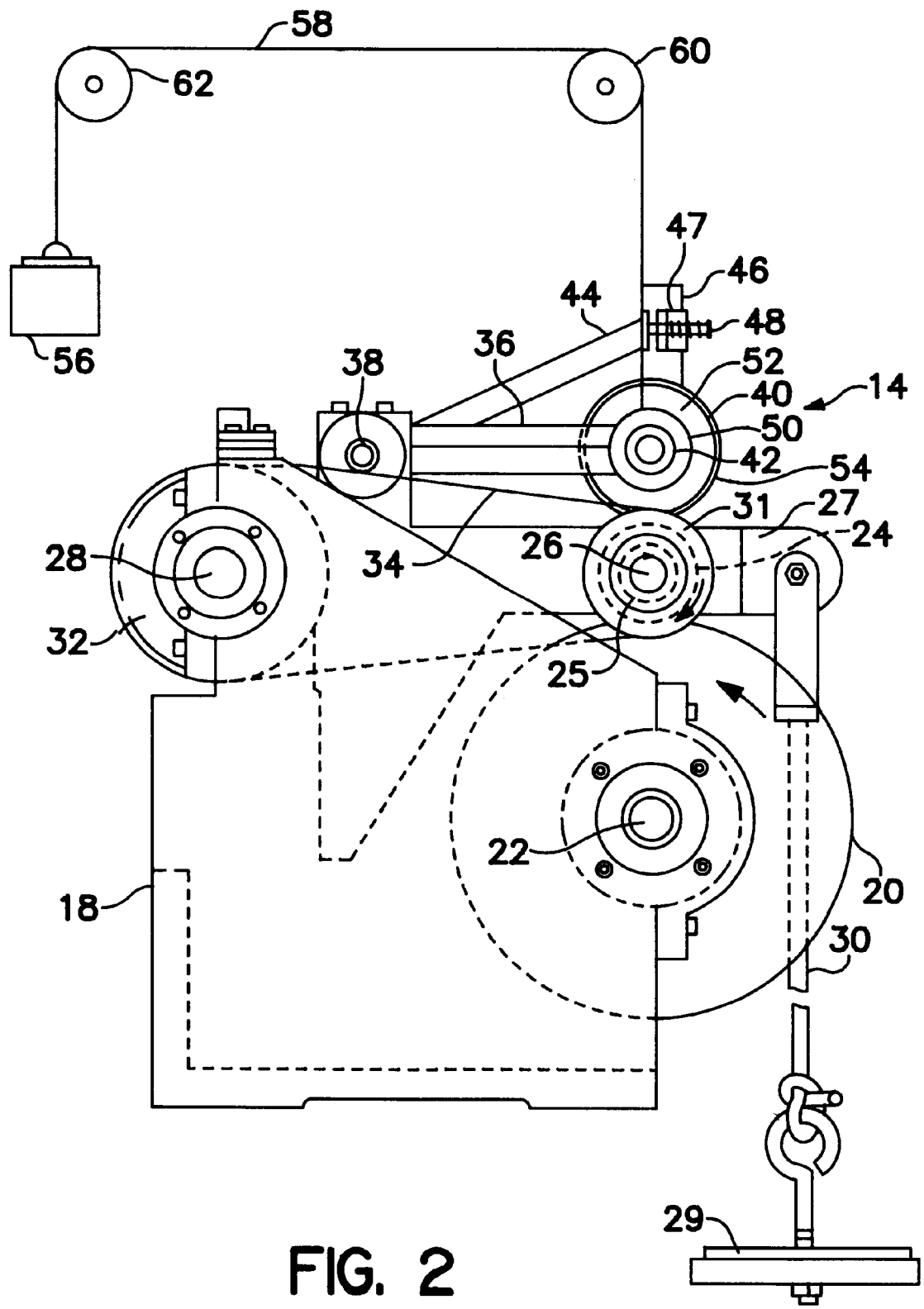

FIG. 2 illustrates a side view of one test station 14 of the abrading apparatus 10 of FIG. 1. Each test station includes a grindstone 20 that is keyed to a grindstone drive shaft 22. In addition, the test station includes a sample wheel 24 that is keyed to a sample wheel drive shaft 26 immediately above the grindstone. The sample wheel may include a steel core 25 (shown in phantom) and a layer of sample material compression molded over the steel core. The sample material may be, for example, a carbon black containing tire tread compound. The sample wheel is molded using techniques known to those of skill in the art.

As shown in FIG. 2, the sample wheel drive shaft 26 is journaled to a free end of a sample wheel frame 27. The sample wheel frame is pivoted about a second sample wheel drive shaft 28, to move the sample wheel 24 into and out of engagement with the grindstone 20. A normal force of the sample wheel against the grindstone is controlled by a counter-weight 29 that is suspended from the free end of the sample wheel frame by a cord 30. The test station 14 also includes a first sprocket 31, which is keyed to the first sample wheel drive shaft adjacent to the sample wheel. A second sprocket 32 is keyed to the second sample wheel drive shaft and is located in-line with the first sprocket. A sample wheel drive belt 34 is mounted over the first sprocket and the second sprocket to drive the sprockets and, therefore, to drive the sample wheel. As shown in FIG. 1, the second sample wheel drive shaft is coupled to the drive module 16, and thus the drive module drives the sample wheel 24.

Each test station 14 also includes a dust wheel frame 36, journaled at one end to the sample wheel frame 27 by a bearing support 38. A dust transfer wheel 40 is journaled at a free end of the dust wheel frame by a bearing support 42 and, as is shown in FIG. 2, is engageable with the sample wheel 24. The dust wheel frame is therefore pivoted about the bearing support to move the dust transfer wheel into and out of engagement with the sample wheel.

The test station further comprises a chalk stick arm 44, which is pivotally mounted at one end to the sample wheel frame 27, adjacent to the dust wheel frame 36. A chalk stick 46 is mounted at a free end of the chalk stick arm 44 by a bracket 47. A free end of the chalk stick is maintained in engagement with the dust transfer wheel 40, under the weight of the chalk stick and the chalk stick arm 44. A rubber band 54, having a width that is about a same width as a rubber core 50 of the dust transfer wheel 40, is fitted around a foam outer layer 52 of the dust transfer wheel. The rubber band is maintained in engagement with the both the sample wheel 24 and the bottom end of the chalk stick. The rubber band receives chalk dust from the chalk stick and, in turn, transfers the chalk dust to the outer surface of the sample wheel. The chalk dust is provided to control a surface condition of an interface between the sample wheel and the grindstone. In particular, the chalk dust is used to ensure wear of the sample under test.

A drawback of the dust transfer wheel assembly is that it does not uniformly dispense the chalk dust to the interface of the grindstone and the sample wheel. If there is insufficient chalk dust, an oily layer of degraded sample material builds up on the abrading surface of the grindstone 20, and decreases the rate of abrasion of the sample wheel 24. In contrast, if too much chalk dusk is provided, the dust can prevent effective contact between the sample wheel 24 and the grindstone 20, and thus decreases the rate of abrasion of the sample wheel 24. It is, therefore, desirable to be able to deliver a uniform amount of chalk dust to the grindstone and sample wheel. In addition, it may be desirable to vary a rate of the chalk dust delivered while ensuring that delivery of the chalk dust is uniform so as to simulate different road conditions, which is not possible with the related art apparatus.

In addition, it is known in the art that temperature is an important factor for rubber degradation. For example, rubber degradation increase with increasing temperature. Therefore, proper simulation of a realistic bulk temperature and surface temperature of the sample wheel is a requirement for a good lab abrasion test. The apparatus 10 includes several heaters 64, as shown in FIG. 1, which are mounted within the cabinet 12 to heat the interior of the cabinet. Thermocouples 65 are also mounted within the cabinet and are coupled to the heaters by wires 66, to control the heaters and maintain a desired temperature within the cabinet.

It is desirable to maintain a steady state temperature that is not too high within the cabinet 12 because the wear rate of sample wheels can change with running temperatures. However, as will be discussed in more detail below, the related art apparatus employs a rotational scheme of sample wheels 24 amongst the plurality of stations 14 and tests each sample wheel on a test station for only a few minutes. The rotational scheme prevents the sample wheels from being tested under a steady state bulk temperature and thus the related art apparatus relies upon the heaters and the thermocouples to provide the steady state temperature.

In addition, the related art steady state temperature is typically set to a temperature of, for example, 50° C. However, the continuous wear rate level of the related art apparatus tends to heat the sample wheel to a temperature range such as, for example, 40°–50° C. above the steady state temp resulting in the bulk temperature of the sample wheels being too hot and in a wear rate of the sample wheels that does not correlate well with actual road wear performance.

The drive module 16 of the related art apparatus 10 also includes a gear that can be removed from the gear shaft and replaced by a different size gear to change a gear ratio of the drive module. The gear ratio controls a ratio of a velocity of the sample wheels 24 to a velocity of the grindstones 20, and is adjustable by manually selecting and replacing different size gears. The rate of abrasion of each sample wheel 24 in each test station 14 is achieved with the related art apparatus by controlling the ratio of the linear velocity of the sample wheels 24 to the linear velocity of the grindstone, which is also referred to as the slip value (S). The slip value S is defined as:

$$S = \frac{V_S - V_G}{V_G} * 100(\%) \quad (1)$$
$$= [V_S / V_G] - 1,$$
$$= [D_S / D_G] \cdot [\Omega_S / \Omega_G] - 1,$$

where $V_S$ is the linear velocity of the sample wheel 24, $V_G$ is the linear velocity of the grindstone, $D_S$ is the diameter of the sample wheel, $D_G$ is the diameter of the grindstone, and $\Omega_S/\Omega_G$ is the gear ratio.

Referring to equation (1), the gear ratio $\Omega_S/\Omega_G$ is usually chosen first and the slip S is then determined by the diameter ratio $D_S/D_G$. Thus, to change the slip ratio S, the gear of the drive module has to be manually changed. Thus, a drawback of the gear and drive shaft arrangement of the related art abrading apparatus 10 is that the apparatus only allows for discrete values of constant slip between the sample wheels and the grindstone. Another drawback of the related art apparatus is that the apparatus is labor intensive. For example, in order to vary the discrete values of slip, the apparatus requires the gear to be manually removed and replaced by a different gear.

In addition, the method of abrading samples of tire compounds with the related art apparatus includes, for example, runner sample wheels (runners) from each of three groups of sample wheels molded from a different tire tread compound. Additional sample wheels from each of the three groups are also used as dummies. The dummies are abraded during a conditioning step of the test, and are maintained within the apparatus while abrading the runners. The dummies are weighed when the runners are weighed during the test, and the weight gain or loss for the dummies is used to correct or adjust the measured weight gain or loss of the runners. The related art apparatus includes a balance accurate to about 0.1 mg that is used to weigh the sample wheels, and a laser micrometer that is used to measure diameters of the sample wheels.

More specifically, the runner sample wheels from each of the three groups are placed on a plurality of spindles in a random order, with six sample wheels per spindle. The dummy sample wheels are placed on separate spindles. A spindle of six sample wheels is tested on a group of six test stations. The runner sample wheels and the dummy sample wheels are conditioned prior to testing, for example, by heating the wheels to a steady state condition. The diameters of the runner sample wheels are measured as described above. The weight of each of the runner sample wheels and the dummy sample wheels are then measured and recorded to the nearest 0.1 mg. The apparatus is then preheated to a desired temperature and the spindles of sample wheels, including both the runners and the dummies, are heated inside the apparatus.

The runners from each spindle are then mounted on the respective sample wheel drive shaft 26 of the six test stations for each group of test stations in a predetermined order. The gear of the drive module is selected to provide a first slip value of, for example, approximately 7% and all of the runners are abraded for a predetermined duration of time such as, for example, for 20 minutes. The runners are then removed from the test stations and placed back on the spindle such that each runner when removed from the spindle of runners will be abraded in a new test station. When the runners are taken off of each test station 14 they are flipped over and placed on the spindle such that the direction of rotation of the runners is reversed. The runners are then mounted onto the respective test stations and abraded for a predetermined number of revolutions at the first slip ratio. The process is repeated six times such that each spindle of sample wheels is abraded on six different test stations. Accordingly, each sample wheel is abraded on each of the grindstones 20 of a group of test stations of the apparatus. After the six rotations between test stations, the runners are mounted on the spindles in the same order as prior to the initiation of the run.

Once all the sample wheels have been removed from the apparatus, they are cooled to room temperature, and the diameter of each runner, and the weights of all the sample wheels, including the runners and the dummies, are again measured and recorded as described above. The average weight loss or gain due to, for example, precipitation for all of the dummies of each compound is subtracted from or added to the weight loss or gain of the runners of each of the respective compounds.

The gear of the drive module is then changed to provide second and third slip values that are, for example, about 13% and about 21% respectively, and the above steps are repeated. The runners may be abraded at the 21% abrasion ratio, for example, for approximately 2 minutes. The 7%, 13% and 21% slip values are selected because they have been found to provide a correlation with road test results. The diameter of each runner, and the weight of both the runners and the dummies, are then measured and recorded, as described above. As can be seen from the above description the manual control of the related art apparatus yields a loss of test time and also requires constant attention by the operator.

Based on data resulting from the abrasion, a wear resistance of the tire tread compound is then computed. In particular, the wear rate (W) of each compound is calculated for each slip value. The wear rate (W) is an average volume loss per unit of travel (cc/cm) of the runners for each given compound. The volume loss (cc) is determined based on the measured weight loss of each runner (corrected based on the weight change of the dummies) and a density of the compound. The travel of each runner at each slip value is calculated by determining an average of each runner's diameter measurement before abrasion and a runner's diameter measurement after abrasion at the slip value. The average diameter measurement is then used to determine the average circumference of the runner at the slip value. The average circumference is then multiplied by the number of revolutions, to determine the travel of the runner at the slip value. The average wear rate at one slip value can then be calculated.

A drawback of the method and apparatus of the related art is that the test is performed for a limited number of constant slip ratios and thus there is no ability to simulate intermittent conditions that exist under actual driving conditions. Others drawbacks are that there is a variability of wear rate amongst the plurality of stations such as, for example, in the range from 30% to 50%. In addition, the complicated scheme of sample wheel rotation amongst all the stations requires time and attention of an operator and, prevents the sample wheels from being tested at the bulk temperature. Further, there is a need to remove and weigh the sample wheels in order to determine the wear rate for each slip value. Still further, there is a need to change the gear of the drive module in order to provide different constant slip ratios. Thus, the method and apparatus is not automated and requires stopping the test in order to make measurements. Moreover, because an average value of weight loss and an average value of travel are used, there are limitations to the accuracy in the predicted wear rate.

Accordingly, it is an object of the present invention to improve upon the methods and apparatus of the related art.

SUMMARY OF THE INVENTION

According to one aspect of the present invention, an automated apparatus for testing at least one sample wheel includes a grindstone drive shaft that rotatably holds a grindstone and a first programmable servo motor coupled to the grindstone drive shaft that drives the grindstone at a plurality of angular velocities. In addition, the automated apparatus includes at least one sample wheel drive shaft disposed about a circumference of the grindstone. Each sample wheel drive shaft of the at least one sample wheel drive shaft rotatably holds a corresponding sample wheel and movably engages and disengages the corresponding sample wheel with the grindstone. Further, the automated apparatus includes a second programmable servo motor coupled to each sample wheel drive shaft. The second programmable servo motor drives each corresponding sample wheel at a plurality of angular velocities to provide a plurality of slip ratios between each corresponding sample wheel and the grindstone.

This embodiment of the automated apparatus may also include a first optical encoder that detects the angular velocity of the grindstone and that outputs a first output signal indicative of the angular velocity of the grindstone, and at least one second optical encoder that detects the angular velocity of a corresponding sample wheel and provides a second output signal indicative of the angular velocity of the corresponding sample wheel.

This embodiment of the automated apparatus may also include a controller that outputs a control signal to each of the first programmable servo motor and the second programmable servo motor to provide the plurality of slip ratios. The controller may also include a means for varying the plurality of slip ratios to simulate a plurality of road conditions. In addition, the controller may also include a means for computing, in situ, a free rolling diameter of each corresponding sample wheel so as to precisely control the slip ratio between each corresponding sample wheel and the grindstone. For this embodiment, the controller is responsive to each of the first output signal and the second output signal. Further the controller may also include a means for determining, in situ, a wear rate of each sample wheel. Still further, the controller may also include a means for averaging out any noise of the system present in either of the first output signal and the second output signal. Moreover, this embodiment may also include a rotating variable powder delivery system that provides a uniform amount of aerosol powder to each sample wheel at any of a plurality of pumping rates which can be used to simulate a plurality of road dust conditions.

Figure 3:
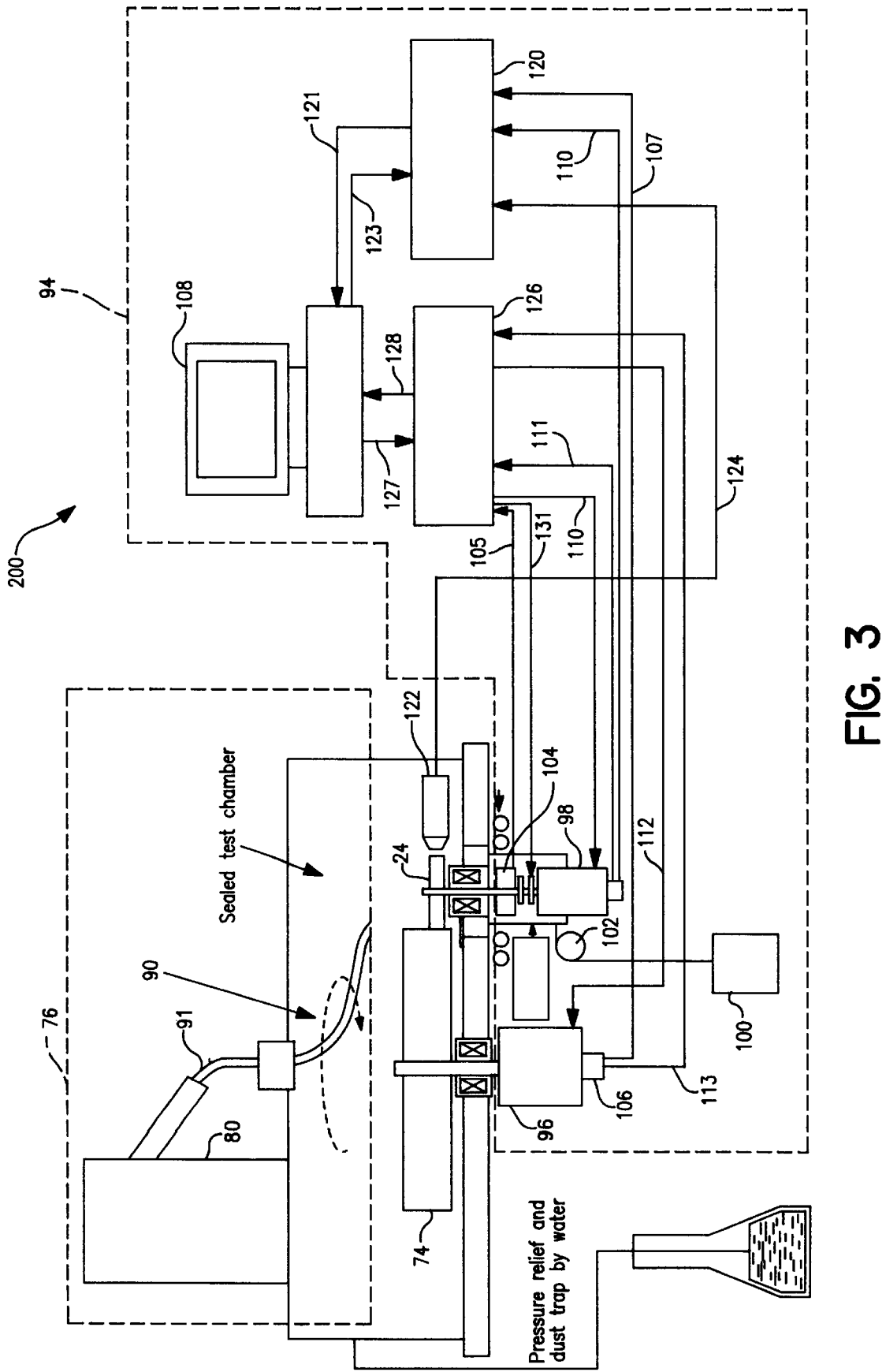
Figure 4:
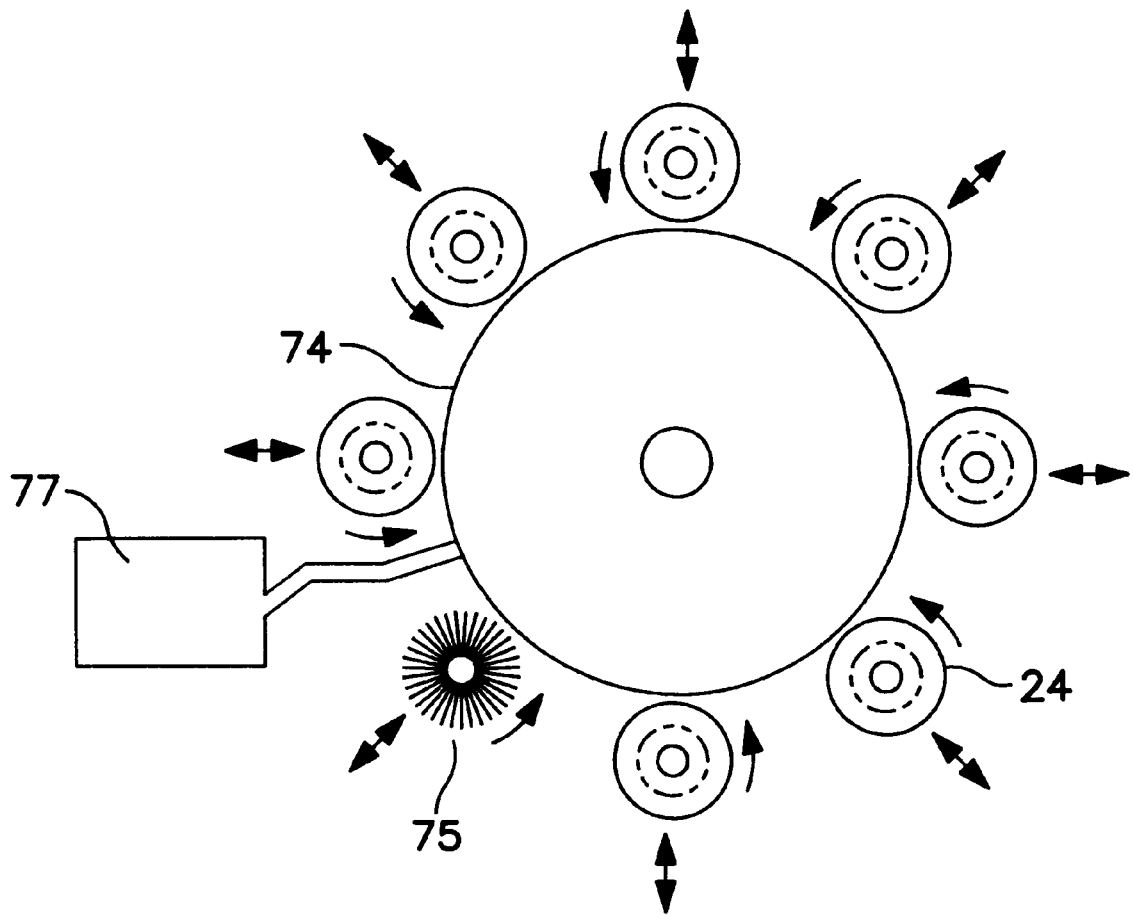
Figure 5:
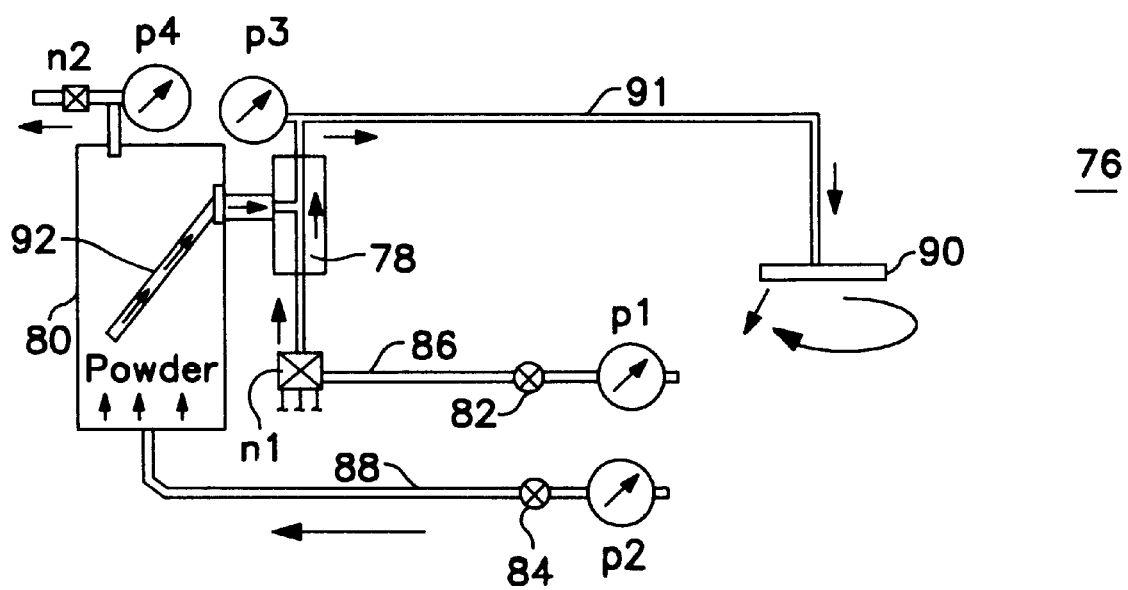

With this embodiment, the automated apparatus of the present invention is automatically controlled and therefore does not require constant manual attention. In addition, the automated apparatus uses a single grindstone wheel to test each sample wheel and therefore eliminates any variability of wear rate amongst a plurality of sample wheels. Further, the automated apparatus provides a uniform amount of dust to each sample wheel at a plurality of pumping rates and thus can uniformly simulate road dust to each of the sample wheels at a plurality of road dust conditions. Still further, the automated apparatus provides a plurality of slip ratios between each sample wheel and the grindstone to simulate a plurality of road conditions. Moreover, the automated apparatus can precisely control the plurality of slip ratios between each sample wheel and the grindstone by determining, in situ, a free rolling diameter of each sample wheel. Furthermore, the automated apparatus of the present invention can determine, in situ, a wear rate of each sample wheel.

Other objects and features of the present invention will become apparent from the following detailed description when taken in connection with the following drawings. It is to be understood that the drawings are for the purpose of illustration only and are not intended as a definition of the limits of the invention.

BRIEF DESCRIPTION OF THE DRAWINGS

The foregoing and other objects and advantages will be more fully appreciated from the following drawings in which:

FIG. 1 illustrates a partial front view of an abrading apparatus of the related art;

FIG. 2 illustrates a side view of a test station of the abrading apparatus of FIG. 1 taken along section line A—A;

FIG. 3 is a perspective view of an abrading apparatus of the present invention;

FIG. 4 is a top plan view of the automated apparatus of FIG. 3, illustrating a single grindstone and a plurality of sample wheels disposed about the circumference of the grindstone;

FIG. 5 illustrates a schematic view of an embodiment of an aerosol powder delivery system according to an embodiment of the present invention;

FIG. 6 illustrates a programmable slip control system according to an embodiment of the present invention; and FIG. 7*a* illustrates a plurality of slip level scenarios and durations which may occur under various actual driving conditions;

FIG. 7*b* illustrates a plurality of simulation scenarios that can be provided by the apparatus of the present invention to simulate the actual driving conditions of FIG. 7*a*, for testing the sample wheels;

FIG. 7*c* illustrates a single cycle slip operation that can be achieved with the slip control system and PC controller of the present invention; and FIG. 8 illustrates the results of an abrasion test on three sample wheels using the abrading apparatus of the present invention.

DETAILED DESCRIPTION OF THE INVENTION

FIG. 3 is a perspective view of an embodiment of an abrading apparatus according to the present invention. The abrading apparatus includes a grindstone 74 and a plurality of sample wheels 24 spaced around a diameter of the grindstone. In addition, the apparatus includes a slip control subsystem 94, as will be discussed infra, that provides the capability to provide a variable slip ratio between each of the sample wheels and the grindstone and to measure a free rolling diameter of each of the sample wheels in situ. Further, the apparatus includes an aerosol powder delivery subsystem 76, as will be discussed infra, that provides a uniform amount of powder to an interface of each of the sample wheels and the grindstone to provide a uniform wear rate of each of the sample wheels under test.

FIG. 4 is a top-plan view of a portion of the apparatus 200 of FIG. 3. The test station includes the grindstone 74 and the plurality of sample wheels 24. As discussed above with respect to the related art (See FIG. 2), each sample wheel may comprise a steel core 25 (shown in phantom) and a layer of sample material compression molded over the steel core using techniques known to those of skill in the art. The sample material may be, for example, a carbon black containing tire tread compound.

In a preferred embodiment of the apparatus 200 of FIG. 4, the grindstone 74 has a diameter of about 18 inches, which is suitable for spacing seven 1.75 inch diameter sample wheels 24 evenly around a circumference of the grindstone. In addition, the apparatus includes a brush 75 that may be brought into contact with and out of contact with, the outer perimeter of the grindstone and a vacuum 77 for removing debris from the apparatus that results from the brush cleaning the surface of the grindstone. In a preferred embodiment, the brush and vacuum are used periodically such as, for example, before measuring the free rolling diameter a plurality of sample wheels. It is to be appreciated that various alterations and modifications may be made to the apparatus shown in FIG. 4 as known to one of skill in the art, and are intended to be within the scope of the present invention. For example, a diameter size of the grindstone and/or of the sample wheels can be varied. In addition, a various number of sample wheels can be used and need not be equally spaced about the circumference of the grindstone.

An advantage of the single grindstone of the present invention is that the same surface is used to abrade each of the sample wheels. This eliminates any variability of the wear rate amongst the plurality of sample wheels and the need to rotate the sample wheels amongst the plurality of test stations, such as in the apparatus of the related art. Therefore, the rotational scheme of the related art abrading apparatus is not needed.

FIG. 5 illustrates a schematic of an embodiment of the aerosol powder delivery subsystem 76 of the apparatus of FIG. 3, according to the present invention. The system includes a venturi 78, a pneumatic fluidizing chamber 80, a first supply line 86, a second supply line 88 and a rotating delivery line 90. The supply to each of the first supply line and the second supply line is controlled by on-off valves 82, 84 respectively, and is monitored by pressure gauges p1, p2. In addition, the aerosol powder delivery subsystem includes a needle valve n1 for controlling a flow rate in the venturi which determines a rate at which an aerosol inside the pneumatic fluidizing chamber is pumped out of the pneumatic fluidizing chamber. A needle valve n2 is used to bleed out any excess air in the pneumatic fluidizing chamber. The venturi creates a negative pressure inside the pneumatic fluidizing chamber thereby pumping, via a tube 92, the aerosol within the pneumatic fluidizing chamber into the rotating delivery line via the venturi and line 91. Pressure gauges p3 and p4 are used to respectively monitor the pressure in lines 91 and the pneumatic fluidizing chamber. The rotating delivery line rotates about all of the sample wheels and dispenses the aerosol in a geometrically uniform fashion to allow a uniform powder delivery to all of the sample wheels 24. It is to be appreciated that by uniform it is meant that a substantially equal amount of powder. With this arrangement, the rate of the aerosol to the sample wheels can be varied so as to, for example, simulate different road dust conditions.

An advantage of the aerosol powder delivery system of the present invention is that it provides uniform powder delivery to each of the sample wheels. Therefore, the abrader of the present invention does not suffer from the variability of wear rate problems due to, for example, non-uniform dispension of the powder amongst a plurality of test stations, or due to a variability in abrading surfaces amongst the plurality of test stations as in the related art apparatus. In addition, another advantage of the system of the present invention is that the system can be controlled to vary the delivery rate of the powder and thus can be controlled to simulate a plurality of different road dust conditions for testing of the sample wheels. However, it is to be appreciated that in a preferred embodiment of the aerosol powder delivery subsystem, the delivery rate of the powder is held constant to ensure that there is sufficient powder between the sample wheels and the grindstone to provide for wear of the sample wheels, since the powder is needed to produce wear of the sample of the wheels.

As discussed above, a rate of abrasion of each sample wheel 24 of each test station 14 of the related art abrading apparatus, is set by controlling the ratio of the linear velocity of the sample wheel 24 to the linear velocity of the grindstone, which is also referred to as the slip ratio (S). The slip value (S) is defined as:

$$\begin{aligned} S &= \frac{V_S - V_G}{V_G} * 100(\%) \\ &= [V_S / V_G] - 1, \\ &= [D_S / D_G] \cdot [\Omega_S / \Omega_G] - 1, \end{aligned} \quad (1)$$

where $V_S$ is the linear velocity of the sample wheel 24, $V_G$ is the linear velocity of the grindstone, $D_S$ is the diameter of the sample wheel, $D_G$ is the diameter of the grindstone, $D_S/D_G$ is the diameter ratio and $\Omega_S/\Omega_G$ is the gear ratio.

As discussed above, the related art abrading apparatus 10 includes the drive module 16 that includes a gear that can be manually removed from the gear shaft and replaced by a different gear to change the gear ratio of the drive module. Referring to equation (1), the gear ratio is usually chosen first and the slip ratio (S) is then determined by the diameter ratio. Thus, a drawback of the gear and drive shaft arrangement of the related art abrading apparatus is that the apparatus only allows for discrete values of constant slip between the sample wheels and the grindstone. However, it is desirable to provide mixed slip road wear simulation capabilities, wherein any number of a plurality of slip ratios can be provided and can be varied with time. In other words, by providing a mixed slip ratio that is variable with time, road wear conditions can be better simulated. The manual gear and drive shaft arrangement of the related art apparatus does not allow for this capability.

Referring to FIGS. 3 and 6, one embodiment of the slip control sub-system 94 of the apparatus of FIG. 3 is shown in detail in FIG. 6. The slip control system includes programmable servo motors 96 and 98 which drive the grindstone wheel 74 and the sample wheels 24, respectively. It is to be appreciated that the programmable servo motors 96 and 98 can be either one of a DC servo motor or an AC servo motor. A normal force of each sample wheel 24 against the grindstone 74 can be controlled, for example, by a counter weight 100 suspended from the sample wheel via a pulley arrangement 102. Thus, a contact force by each sample wheel 24 against the grindstone 74 can be adjusted by adjusting the weight of the counter weight. Although the force of the sample wheel against the grindstone can be controlled by the counter weight 100, it is to be appreciated that in the preferred embodiment of the present invention, as will be discussed in greater detail below, the wear rate of each sample wheel is controlled via the programmable servo motors and the PC controller to provide variable slip rates between the sample wheels and the grindstone.

The system of FIG. 6 also includes optical encoders 104 and 106 that detect an angular velocity of each of the sample wheels and the grindstone, respectively. The optical encoders record the angular displacement of the sample wheels and the grindstone at regular intervals to determine the rotational speed of the sample wheels and the grindstone. The angular velocity information may also be made available via an analog signal output by tachometers via respective lines 105, 107 to a Fluke 2645A Net DAQ™ multichannel recorder 120 available from the Fluke Corporation, P.O. Box 9090, Everett, Wash. 98206-9090. In particular, the sensor receives count signals from each of the optical encoders and communicates the count information to and with the PC controller 108 via lines 121, 123. The angular displacement information is translated by the PC controller into distance traveled by the sample wheels and the grindstone which, as will be discussed in greater detail below is ultimately used to compute the wear rate of the sample wheels. In a preferred embodiment the slip control subsystem includes at least one surface temperature sensor 122 that monitors a surface temperature of the sample wheels and outputs the surface temperature information to the sensor 120 via line 124.

The PC 108 controls the programmable servo motors 98 and 96, via lines 110 and 112 respectively, to precisely control the angular velocities of the sample wheels and the grindstone. A preferred embodiment of the slip control system 94 includes IMC-S 204 iCODE Version 2.1 Motion Controller 126 including Graphic Motion Language software version 3.6 available from Alan Bradley, a Rockwell International Co., 1201 South Second Street, Milwaukee, Wis. 53204. The Alan Bradley controller is interfaced to and controlled by custom software stored and executed on the PC that is output to the controller and that communicates with the controller via lines 127–128 to instruct the Alan Bradley controller to vary the angular velocities of one or both of the programmable servo motors 96 and 98 to vary the slip ratio between the grindstone and the sample wheels.

An advantage of the slip control system and PC controller of the present invention is that the system is automated and thus does not suffer from the manual requirements of the related art abrading apparatus. In particular, as will be discussed in greater detail below, the system automatically can provide a plurality of mixed slip ratios to simulate a plurality of road wear conditions. In addition, as will be discussed below, the system and PC controller provide precision and stability that is not available with the related art automated abrading apparatus, or with analog control electronics.

Referring to Equation (1), in order to provide an accurate slip value S, a ratio of the diameter ratio $D_S/D_G$ must be accurately known. According to the present invention, a concept of a free rolling diameter D, wherein the sample wheels are not engaged with the programmable motor, is defined as twice of the total distance traveled $\Delta x$ divided by a total angle of rotation $\Delta\theta$, or:

$$D = 2 \cdot \Delta x / \Delta\theta. \quad (2)$$

In a preferred embodiment of the invention, the sample wheels are disengaged from the programmable motor 98 at regular intervals to measure the free rolling diameter of the sample wheels. In particular, the slip control subsystem 94 includes an electromagnetic clutch 130 (See FIG. 6) that is controlled via the motion controller 126 and the PC controller 108 through control line 131 (See FIG. 3), that engages and disengages the programmable motor 98 from the sample wheels 24 to allow the sample wheels to freely roll with minimal internal friction. The slip control subsystem also includes pressurized bearing housings 132, 134 which help to protect the bearings of the programmable motors from dust contamination and thus to prevent the bearings from wearing out.

When there is no slip between the sample wheels and the grindstone, the total distance traveled for each is the same, or:

$$\Delta X_S = \Delta X_G; \text{ and } \Delta\theta_S \cdot D_G/2 = \Delta\theta_G D_S/2 \tag{3}$$

Figure 6:
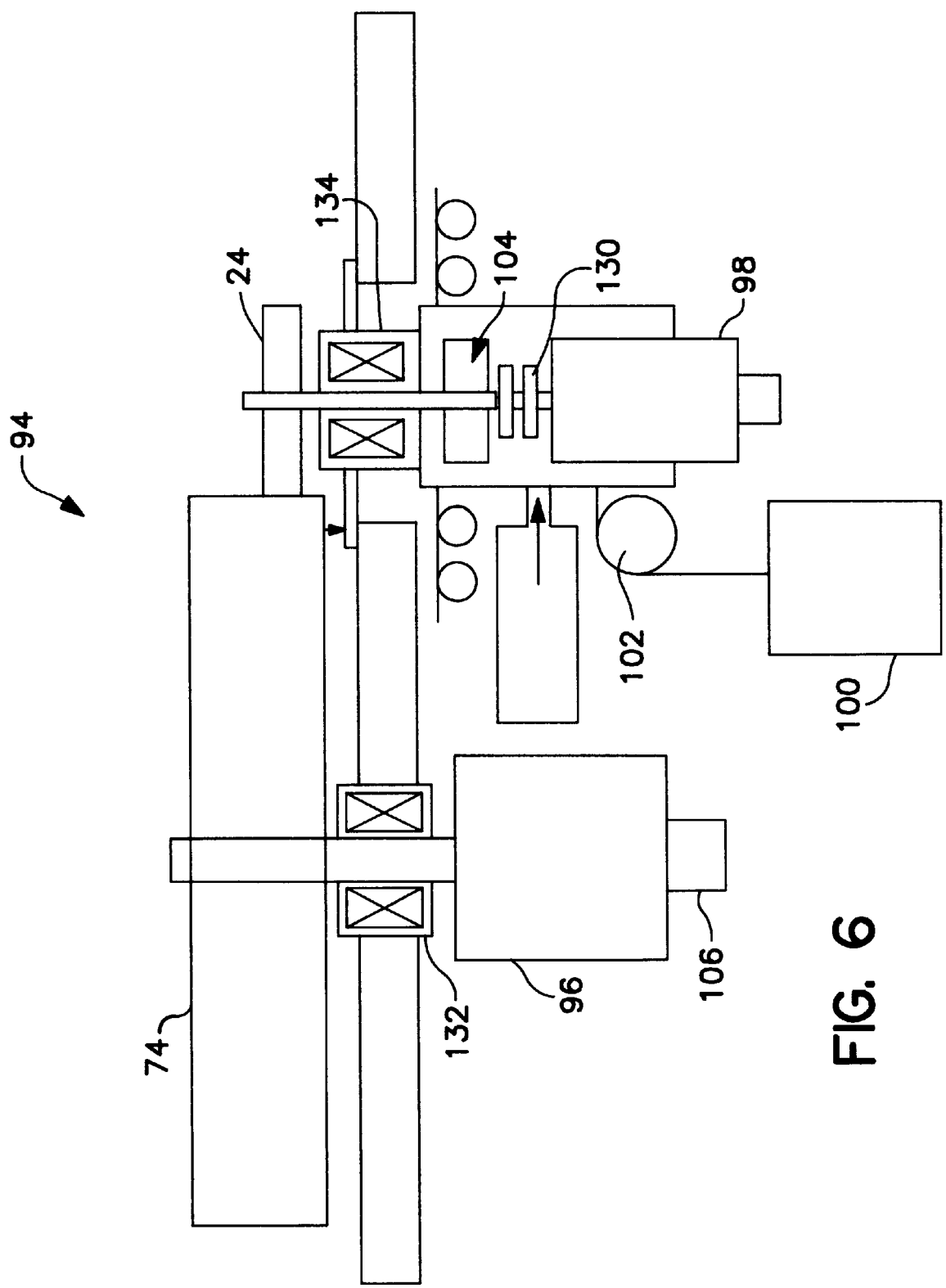

In equation (3), the diameter of the grindstone $D_G$ is a constant, and the ratio of the total distance traveled by each of the grindstone and the sample wheel ($\Delta\theta_G/\Delta\theta_S$) can be measured by the optical encoders 104 and 106 as discussed above with respect to FIGS. 1 and 6. Therefore the free rolling diameter of the sample wheels $D_S$ and from this the slip values S between each sample wheel and the grindstone, can be accurately determined.

For example, in the preferred embodiment of the present invention the diameter ratio, $D_S/D_G$, is 18/1.75, or approximately 10.3. Assuming the grindstone makes 20 revolutions, and assuming that for each resolution of the grindstone, the optical encoder will count 8,000 counts per revolution, then the encoder 106 will count 160,000 resolutions. In the same amount of time that it takes to make 20 revolutions of the grindstone, the sample wheels having a 1.75 inch diameter will make many more revolutions, and the optical encoder may count, for example, approximately 1,600,000 counts. A worst case resolution, due to noise of the system, of the optical count measurement of the grindstone has been measured at three parts per 100,000. Thus, for a 1.75 inch diameter sample wheel, a 1.5 $\mu$m resolution of the rolling diameter measurement is achievable.

In contrast, as discussed above with respect to the related art abrading apparatus, the diameter and weight of each sample wheel, including both runner wheels and dummy wheels, are measured before and after the sample wheels are abraded on the plurality of test stations. For a 0.375 inch× 1.75 inch diameter sample wheel, a weight loss of the sample wheel is typically 150 mg. With an electronic balance and with caution, this weight loss can be measured to within 1% precision, or about 0.1 mg. However, a corresponding change in diameter of the sample wheel is only about 0.1 mm. Thus, a 1% precision measurement of the change in diameter would require a 1 $\mu$m resolution, which is beyond the capability of even a laser micrometer. Therefore, the ability to measure the free rolling diameter according to the present invention allows the diameter ratio to be measured, and the slip ratio to be provided with greater precision than the abrading apparatus of the related art.

Figure 7A:
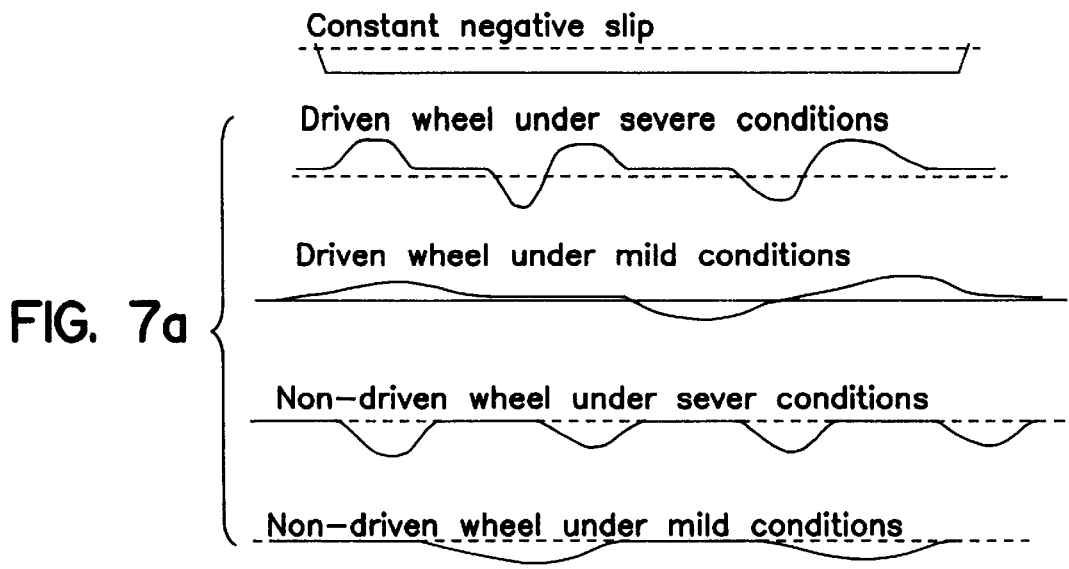
Figure 7B:
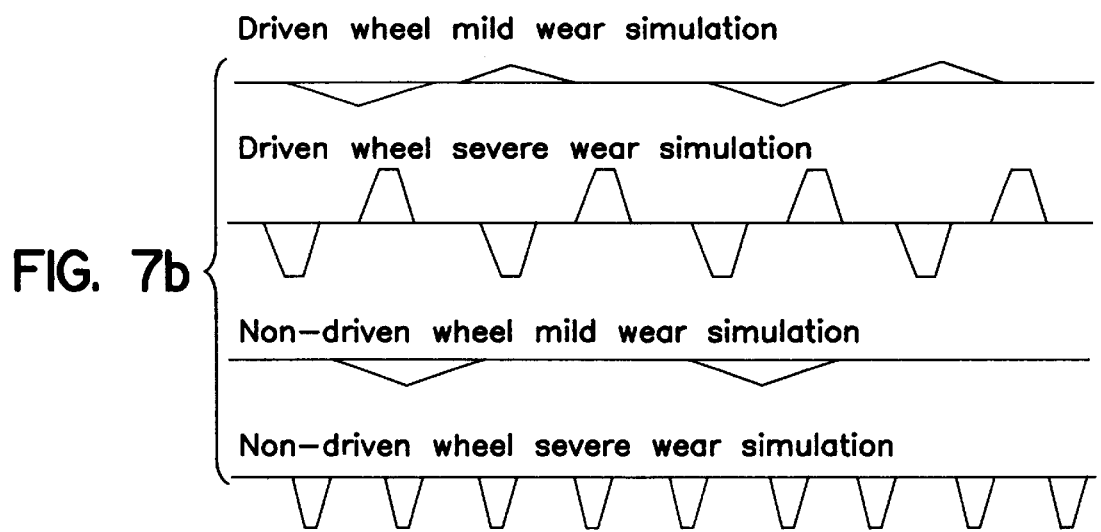
Figure 7C:
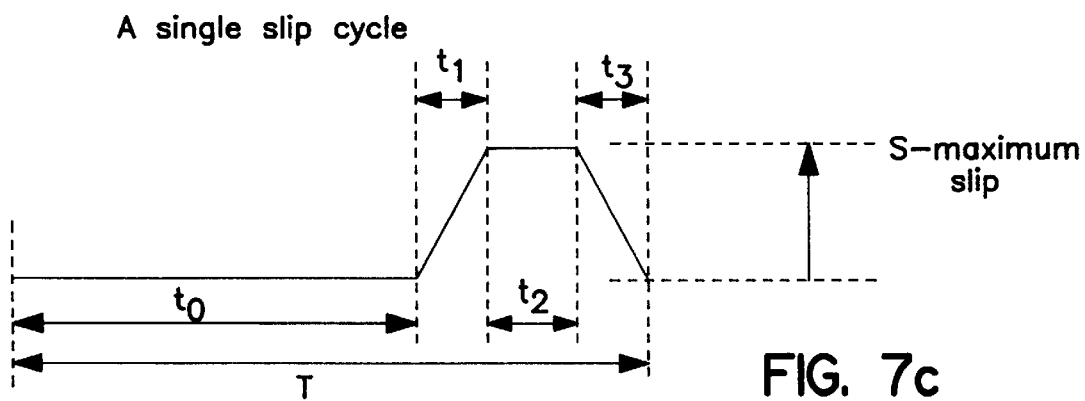
Figure 8:
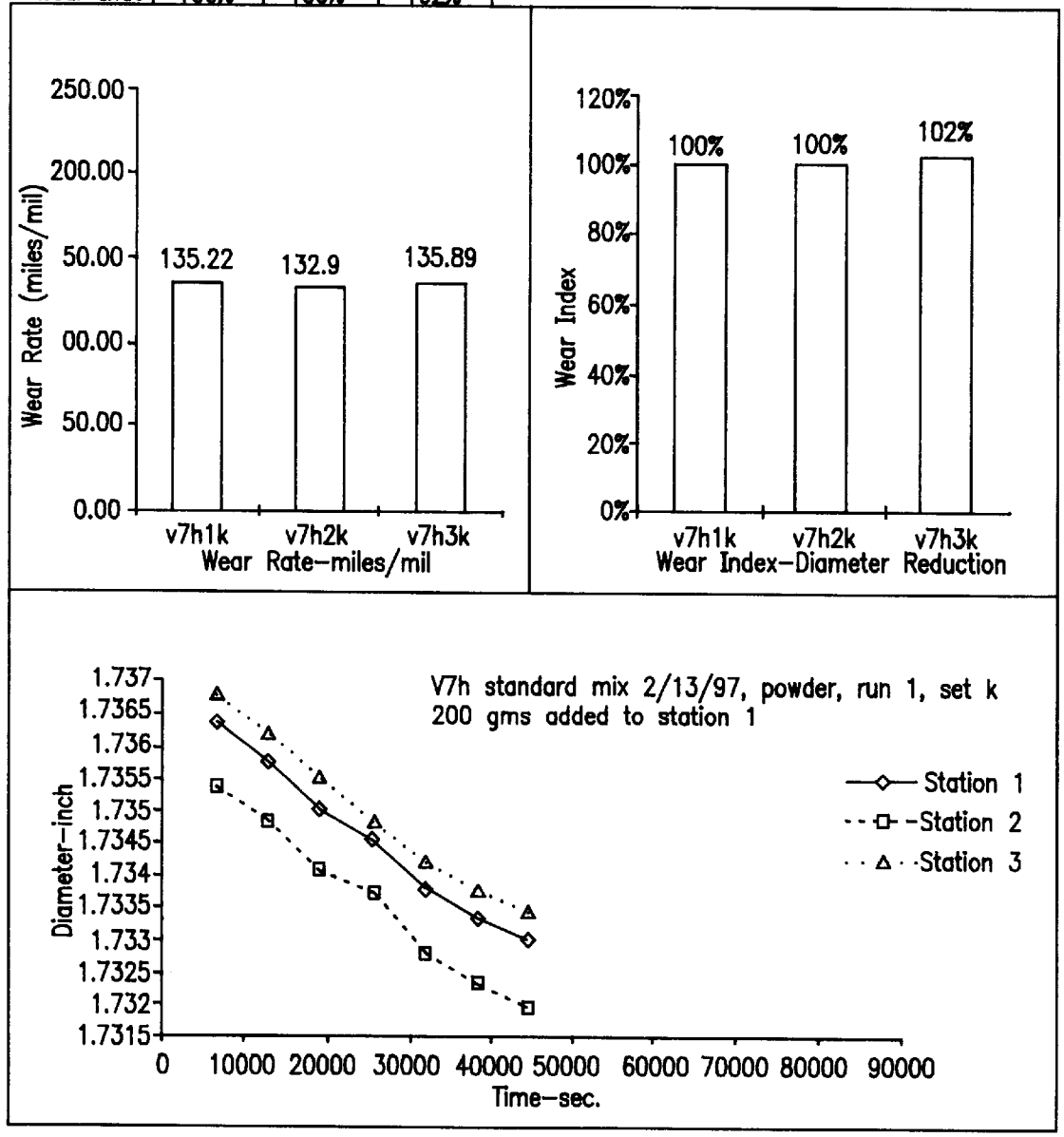

The free rolling diameter of the sample wheels can then be used to calculate the wear rate of the sample wheels. Referring to FIG. 8, there is illustrated the results of an abrasion test on three sample wheels using the abrading apparatus of the present invention. The free rolling diameter of each sample wheel is calculated and plotted as a function of time. In particular, the free rolling diameter is calculated at regular intervals such as, for example, after 100 cycles of a single cycle slip operation such as is illustrated in FIG. 7c. By measuring the free rolling diameter at the regular intervals, the reduction of the sample wheel diameter can be plotted versus time of the test. Since the free rolling diameter of the sample wheel is known, the distance traveled by the sample wheel can also be calculated. For example, if every revolution of a typical passenger tire is a distance traveled of 2 meters, the total number of revolutions over time can be multiplied by 2 meters to calculate the total distance traveled by the tire.

Referring to FIG. 8, the wear rate of each sample wheel can be calculated from the slope of the total diameter reduction of the sample wheel as a function of the distance traveled. Alternatively, the total distance traveled by the sample wheel can be divided by the diameter reduction of the sample wheel to determine the wear rate in units of, for example, miles traveled per mil of diameter reduction of the sample wheel, as is illustrated by the bar graphs in FIG. 8.

Another advantage of the slip control system and PC controller of the present invention is that an averaging technique can be used to improve a signal-to-noise ratio of the free rolling diameter measurements. For example, by measuring the free rolling diameter for a period of time such as, for example, 20 seconds, repeated cycles of the sample wheel can be averaged to eliminate any noises due to, for example, surface roughness, or radial run-out of the sample wheels, and the like.

Still another advantage of the system of the present invention is that the system allows the free rolling diameter to be measured in situ. In other words, the system of the present invention does not suffer the infirmities of the related art abrading apparatus wherein the sample wheels must be weighed prior to abrading and must be manually removed, weighed and measured after abrading. With the system of the present invention the measurement can be made while the test is running and therefore is much less labor and time intensive.

As discussed above, the known methods and apparatus of the related art do not offer good predictions of tread wear performance. In particular, it is generally known that tire tread wear is a two-stage process. In a first stage there is degradation due to fatigue with little or no slip of the tire, and in a second stage there is removal of weakened skin rubber by a larger slip of the tire. In addition, temperature is an important factor for rubber degradation, and thus proper simulation both of the bulk and the surface temperature is necessary for a good lab abrasion test. Furthermore, in modern radial belted tires, slippage of the tire under actual road conditions is very small. For example, large slippage only takes place when driving torque, breaking torque or lateral cornering forces are applied to the tires. Accelerometer data from various driving conditions have shown that slippage usually happens only momentarily, for example, on an order of a few seconds. Thus, on highways, for example, a constant speed mode may occupy 80% to 90% of driving time. In contrast, in city driving, the constant speed mode might be more in the range of approximately 50%. Furthermore, the level of acceleration for each of these conditions is different. Still further, a cornering severity is higher for city and winding secondary road surfaces than for highway driving. Thus, it is evident that constant slip test conditions cannot properly simulate actual road wear results.

It is an advantage of the apparatus of the present invention that each of the above conditions can be simulated with the slip control system and PC controller of the present invention. For example, FIG. 7a illustrates a plurality of slip level scenarios and durations which may occur under various actual driving conditions, and FIG. 7b illustrates a plurality of simulation scenarios that can be provided by the apparatus of the present invention for testing the sample wheels. In particular referring to FIG. 7c, there is illustrated a single slip cycle operation that can be achieved with the slip control system and PC controller of the present invention. The simulated driving conditions such as, for example, illustrated in FIG. 7b can be implemented by varying any of, for example, a period T of the single braking cycle operation, a time $t_0$ of a 0% slip or, in other words, a time of free rolling, a time of ramping up $t_1$ to a maximum slip ratio of S, a time $t_2$ of holding at the maximum slip ratio, and a time for ramping down $t_3$ to the free rolling condition. An abruptness of the braking operation can be simulated, depending on the how hard a driver applies the brake, by the length of $t_1$ and $t_3$. This single slip cycle can then be repeated a number of times as illustrated in FIG. 7b. Thus, the slip control system and PC controller of the present invention offers a flexible apparatus to simulate with precision various road wear conditions, in situ, and to measure with precision the wear rate, in situ.

Having thus described several particular embodiments of the invention, various alterations, modifications, and improvements will readily occur to those skilled in the art. Such alterations, modifications, and improvements are intended to be part of this disclosure, and are intended to be within the spirit and scope of the invention. Accordingly, the foregoing description is by way of example only and is limited only as defined in the following claims and the equivalents thereto.

What is claimed is:

1. An automated apparatus for testing at least one sample wheel, comprising:
    a grindstone drive shaft that rotatably holds a grindstone;
    a first programmable servo motor coupled to the grindstone drive shaft and responsive to a first control signal, that drives the grindstone at a plurality of angular velocities as determined by the control signal;
    at least one sample wheel drive shaft disposed about a circumference of the grindstone, each sample wheel drive shaft of the at least one sample wheel drive shaft rotatably holding a corresponding sample wheel and movably engaging and disengaging the corresponding sample wheel with the grindstone; and
    a second programmable servo motor coupled to each sample wheel drive shaft and responsive to a second control signal, that drives each sample wheel drive shaft at a plurality of angular velocities as determined by the control signal so as to provide a variable slip ratio between each corresponding sample wheel and the grindstone.

2. The automated apparatus as claimed in claim 1, further comprising a controller that outputs the first control signal and the second control signal to control each of the first servo motor and the second servo motor, respectively, to provide the variable slip ratio.

3. The automated apparatus as claimed in claim 2, wherein the controller includes a means for simulating a plurality of road conditions with the automated apparatus and for varying at least one of the first control signal and the second control signal to vary the slip ratio to simulate any of the plurality of road conditions.

4. The automated apparatus as claimed in claim 3, further comprising:
    a first optical encoder disposed adjacent the grindstone that detects the angular velocity of the grindstone and that provides a first output signal indicative of the angular velocity of the grindstone; and
    at least one second optical encoder, each second optical encoder of the at least one second optical encoder being disposed adjacent a corresponding sample wheel, that detects the angular velocity of the corresponding sample wheel and that provides a second output signal indicative of the angular velocity of the corresponding sample wheel.

5. The automated apparatus as claimed in claim 4, wherein the controller includes a processor that is responsive to each of the first output signal and the second output signal and wherein the processor includes a means for computing, in situ, a rolling diameter of each sample wheel.

6. The automated apparatus as claimed in claim 4, wherein the controller includes a processor that is responsive to each of the first output signal and the second output signal, and wherein the processor includes a means for determining, in situ, a wear rate of each sample wheel.

7. The automated apparatus as claimed in claim 5, wherein the processor further includes a means for averaging out any noises of the automated apparatus within the first output signal and the second output signal.

8. The automated apparatus as claimed in claim 6, wherein the processor further includes a means for averaging out any noises of the automated apparatus within the first output signal and the second output signal.

9. The automated apparatus as claimed in claim 1, further comprising a rotating variable powder delivery system that provides a uniform amount of powder to each sample wheel at a plurality of pumping rates.

10. The automated apparatus as claimed in claim 9, wherein the rotating variable powder delivery system includes:
    a pneumatic fluidizing chamber responsive to a first supply line, that holds an aerosol powder and that outputs the aerosol powder at an output tube;
    a venturi responsive to a second supply line and coupled to the output tube, that creates a negative pressure inside the pneumatic fluidizing chamber that results in an outward flow of the aerosol powder from the pneumatic fluidizing chamber to the venturi;
    a first adjustable valve in the first supply line that can be adjusted to vary a rate at which the aerosol powder is output to the venturi; and
    a rotary delivery line coupled to the venturi that rotates about a circumference of the grindstone and that uniformly delivers the aerosol powder to an interface of the grindstone and each sample wheel at the rate determined by the first adjustable valve.

11. An automated apparatus for testing a plurality of sample wheels, comprising:
    a grindstone drive shaft that rotatably holds a grindstone;
    a first programmable servo motor coupled to the grindstone drive shaft and responsive to a first control signal, that drives the grindstone at a plurality of angular velocities as determined by the control signal;
    a plurality of sample wheel drive shafts disposed about a circumference of the grindstone, each sample wheel drive shaft rotatably holding a respective sample wheel and movably engaging and disengaging the sample wheel with the grindstone; and
    a second programmable servo motor coupled to each of the plurality of sample wheel drive shafts and responsive to a second control signal, that drives each of the plurality of sample wheels at a plurality of angular velocities as determined by the control signal so as to provide a variable slip ratio between each of the sample wheels and the grindstone.

12. An automated apparatus for testing at least one sample wheel, comprising:
    a grindstone drive shaft that rotatably holds a grindstone;

a grindstone driving means for driving the grindstone at a plurality of angular velocities;

at least one sample wheel drive shaft disposed about a circumference of the grindstone, each sample wheel drive shaft of the at least one sample wheel drive shaft rotatably holding a corresponding sample wheel and movably engaging and disengaging the corresponding sample wheel with the grindstone; and a sample wheel driving means for driving each sample wheel drive shaft at a plurality of angular velocities to provide a variable slip ratio between each corresponding sample wheel and the grindstone.

13. The automated apparatus as claimed in claim 12, wherein the grindstone driving means and the sample wheel driving means include:

a first programmable servo motor coupled to the grindstone drive shaft and responsive to a first control signal, that drives the grindstone at any of the plurality of angular velocities as determined by the first control signal;

a second programmable servo motor coupled to each sample wheel drive shaft and responsive to a second control signal, that drives each corresponding sample wheel at any of the plurality of angular velocities as determined by the second control signal so as to provide the variable slip ratio; and a controller that outputs the first control signal and the second control signal to control each of the first programmable servo motor and the second programmable servo motor to provide the variable slip ratio.

14. The automated apparatus as claimed in claim 13, wherein the controller includes a means for simulating a plurality of road conditions with the automated apparatus and for varying at least one of the first control signal and the second control signal to vary the slip ratio to simulate any of the plurality of simulated road conditions.

15. The automated apparatus as claimed in claim 14, further comprising:

a first optical encoder disposed adjacent the grindstone that detects the angular velocity of the grindstone and that provides a first output signal indicative of the angular velocity of the grindstone; and at least one second optical encoder, each second optical encoder of the at least one second optical encoder being disposed adjacent a corresponding sample wheel, that detects the angular velocity of the corresponding sample wheel and that provides a second output signal indicative of the angular velocity of the corresponding sample wheel.

16. The automated apparatus as claimed in claim 15, wherein the controller includes a processor that is responsive to each of the first output signal and the second output signal and wherein the processor includes a means for computing, in situ, a rolling diameter of each sample wheel.

17. The automated apparatus as claimed in claim 15, wherein the controller includes a processor that is responsive to each of the first output signal and the second output signal, and wherein the processor includes a means for determining, in situ, a wear rate of each sample wheel.

18. The automated apparatus as claimed in claim 16, wherein the processor further includes a means for averaging out any noises of the automated apparatus within the first output signal and the second output signal.

19. The automated apparatus as claimed in claim 17, wherein the processor further includes a means for averaging out any noises of the automated apparatus within the first output signal and the second output signal.

20. The automated apparatus as claimed in claim 12, further comprising a rotating variable powder delivery system that provides a uniform amount of powder to each sample wheel at a plurality of pumping rates.

* * * * *